US00PP09305P

United States Patent [19]

Stoots

[11] Patent Number: Plant 9,305

[45] Date of Patent: Sep. 26, 1995

[54] VARIETY OF GERANIUM NAMED 'RED HOTS'

[75] Inventor: Eleanor Stoots, Connellsville, Pa.

[73] Assignee: Oglevee, Ltd., Connellsville, Pa.

[21] Appl. No.: 347,583

[22] Filed: Nov. 30, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Webb Ziesenheim Bruening Logsdon Orkin & Hanson

[57] ABSTRACT

The new cultivar is early flowering and maintains a controlled growth habit. It is also free flowering. It is very heat tolerant, recovers quickly after wet weather conditions and still exhibits a neat mound habit. The bloom color is a bright red on a dark green foliage.

1 Drawing Sheet

BACKGROUND OF THE INVENTION

The present invention comprises a new and distinct cultivar of *Pelargonium×hortorum* known by the varietal name 'Red Hots' (Oglevee No. 1395, Breeder No. KB-19-91). The new variety was discovered in a selected breeding program in Connellsville, Pa. on Nov. 19, 1991. The new variety is a selection from the crossing of the commercial variety 'Victoria', U.S. Plant Pat. No. 5,054, (female parent), and the breeding variety, Oglevee No. 8110, (male parent). Following the cross, the embryo was extracted and grown in tissue culture. The new variety was first asexually reproduced by cuttings at Oglevee, Ltd. in Connellsville, Pa. on Jan. 29, 1992. The new variety has been asexually reproduced by cuttings at Oglevee, Ltd. in Connellsville, Pa. over a several year period. It has also been trial and field tested at Connellsville and has been found to retain its distinctive characteristics through successive propagations.

This new variety exhibits the bright red bloom color of the variety 'Victoria' and the dark green foliage color of the male parent. The new variety differs from the parentage in that it has a more vigorous growth habit and is more heat tolerant than either of the parent plants.

The cultivar, when grown in a glass greenhouse in Connellsville, Pa. using natural light and temperatures of 60° F. night and 72° F. day, has a response time of six weeks from a rooted cutting to flowering in a 10 cm pot. The response time was determined on plants grown in soilless media employing constant fertilizer 200 parts per million of nitrogen and potassium in full light. The rooted cuttings were potted on Feb. 23, 1994 and flowered on Apr. 7, 1994 in a 15 cm pot.

DESCRIPTION OF THE DRAWINGS

The accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Pa. The plant history was taken on six week plants blossomed under natural light in a greenhouse and the color readings were taken indoors under 200–220 foot candles of fluorescent cool white light. Color references are primarily to the RHS Color Chart of the Royal Horticultural Society of London.

THE PLANT

Classification:
- *Botanical.*—*Pelargonium×hortorum.*
- *Commercial.*—Zonal florists' geranium.

Form: Semi-dwarf mound.
- *Height.*—14.0–16.0 cm above media surface.
- *Growth.*—Semi-dwarf, free flowering, free branching with semi-double flowers.

Strength: Stands upright without artificial support.

Foliage: Stalked leaf attachment.

Leaves:
- *Size.*—9.0–10.0 cm across; fully expanded leaf.
- *Shape.*—Reniform, cordate base.
- *Margin.*—Crenate.
- *Texture.*—Leathery, pubescent.
- *Color.*—Top: Yellow-Green Group 147A. Bottom: Yellow-Green Group 147B.
- *Ribs and veins.*—Venation: Palmate. Color: Yellow-Green Group 146C.
- *Zone.*—No zone present.

Petioles:
- *Color.*—Yellow-Green Group 146B.
- *Length.*—7.5–11.0 cm.

Stem:
- *Color.*—Yellow-Green Group 146C.
- *Internodes.*—1.0–4.0 cm in length.

THE BUD

Shape: Upright hemispherical cluster.

Size: 2.5–3.5 cm across.

INFLORESCENCE

Blooming habit: Semi-double; free and early flowering; slow to shatter.

Size:
- *Closed florets.*—1.0–1.5 cm.
- *Fully open bloom.*—9.0–12.0 cm across.

Borne: Umbel; florets on pedicel; pedicel on peduncle; 5.0–7.0 cm above the foliage.

Florets:
- *Form.*—Flat to slightly cupped; petaloids present.
- *Color.*—Top: Red group 45B. Bottom: Red group 44C. Eye: Red group 44B.
- *Petals.*—Separate, not united; margin entire; obovate; flat to slightly cupped; 5– 8 in number.
- *Size.*—4.0–4.5 cm across.
- *Texture and appearance.*—Velvety; Appearance from a distance is a rich deep red bloom above a semi-dwarf plant with very dark green foliage.

Petaloids:

*Quantity.*—1–3.

*Shape.*—Some tubular, flat, twisted, some with pollen attached.

*Color.*—Top: Red group 44C at the base to Red Group 45B at the tip. Bottom: Red group 44C.

Pedicel:

*Length.*—1.5–2.0 cm.

*Color.*—Greyed-Purple Group 183B.

Peduncle: 13.0–17.0 cm in length.

*Color.*—Stem end: Yellow Green 146B. Umber end: Greyed-Purple Group 183A.

Disease resistance: Not known.

REPRODUCTIVE ORGANS

Stamens:

*Anthers.*—2.0–3.0 mm in length.

*Filaments.*—5.0–7.0 mm in length. Color: White to slightly pink.

*Pollen.*—Golden brown.

Pistils:

*Number.*—1.

*Length.*—8.0–10.0 mm.

*Stigma.*—5–6 parted; Red purple.

*Style.*—3.0–4.0 mm in length; Red purple.

Ovaries: Superior; pubescent; pale green, 4.0–7.0 mm in length.

Fruit: None observed.

GENERAL CHARACTERISTICS

The 'Red Hots' variety is an improvement over the commercial variety 'Tango' for both the greenhouse grower and the home gardener. For the grower, 'Red Hots' performs well from the rooting stage through production to the market. This variety will flower at least one week earlier, maintains a controlled growth habit and is free flowering. 'Red Hots' in the garden is very heat tolerant, recovers quickly wet weather conditions and still exhibits a neat mound habit.

I claim:

1. A new and distinct variety of geranium plant substantially as shown and described.

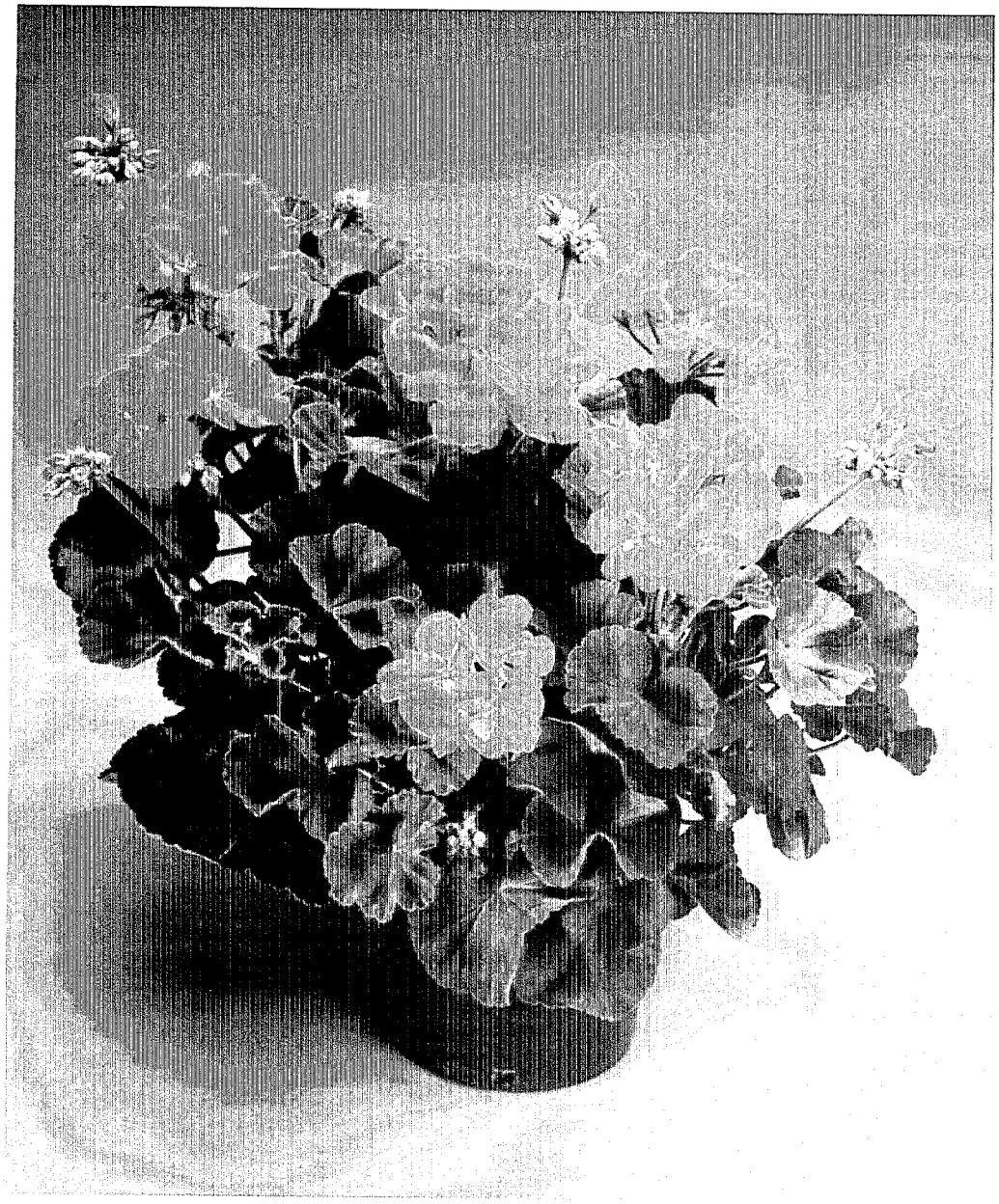

* * * * *